US012678246B2

(12) United States Patent (10) Patent No.: US 12,678,246 B2
Kanazawa et al. (45) Date of Patent: Jul. 14, 2026

(54) SURGICAL ROBOT AND CONTROLLER OF SURGICAL ROBOT

(71) Applicant: RIVERFIELD INC., Tokyo (JP)

(72) Inventors: Masao Kanazawa, Tokyo (JP); Yasushi Tanaka, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 351 days.

(21) Appl. No.: 17/884,981

(22) Filed: Aug. 10, 2022

(65) Prior Publication Data

US 2022/0378536 A1 Dec. 1, 2022

Related U.S. Application Data

(63) Continuation of application No. PCT/JP2021/000555, filed on Jan. 8, 2021.

(30) Foreign Application Priority Data

Feb. 12, 2020 (JP) ................................. 2020-021629

(51) Int. Cl.
*A61B 34/37* (2016.01)
*A61B 34/00* (2016.01)

(52) U.S. Cl.
CPC .............. *A61B 34/37* (2016.02); *A61B 34/25* (2016.02); *A61B 34/74* (2016.02); *A61B 34/76* (2016.02);
(Continued)

(58) Field of Classification Search
None
See application file for complete search history.

(56) References Cited

U.S. PATENT DOCUMENTS 7,695,481 B2 * 4/2010 Wang ..................... A61B 34/75
414/2
10,013,082 B2 * 7/2018 Schecter .............. A61B 5/7455
(Continued)

FOREIGN PATENT DOCUMENTS

CN 101642363 A 2/2010
CN 109496143 A * 3/2019 ............. A61B 34/20
(Continued)

OTHER PUBLICATIONS

C. J. Payne, H. Rafii-Tari, H. J. Marcus and G.-Z. Yang, "Hand-held microsurgical forceps with force-feedback for micromanipulation," 2014 IEEE International Conference on Robotics and Automation (ICRA), Hong Kong, China, 2014, pp. 284-289 (Year: 2014).*
(Continued)

*Primary Examiner* — Khoi H Tran
*Assistant Examiner* — Dairon Estevez
(74) *Attorney, Agent, or Firm* — Sughrue Mion, PLLC

(57) ABSTRACT

A surgical robot includes an operation part that includes a movable part moved by a force applied by an operation by a user, an action part that performs an action according to the operation, a drive part that supplies a driving force to the action part, an operation controller that controls a movement of the movable part, and a controller that implements an operation force setter that sets a magnitude of a resistance force that is a force in a direction opposite to a direction of the movement of the movable part. The operation force setter sets the magnitude of the resistance force based on a resistance parameter set in advance, and the operation controller applies, to the movable part, the resistance force having the magnitude set by the operation force setter.

18 Claims, 9 Drawing Sheets

(52) U.S. Cl.
CPC ........ *A61B 34/77* (2016.02); *A61B 2034/258* (2016.02)

(56) References Cited

U.S. PATENT DOCUMENTS

| | | | |
|---|---|---|---|
| 2007/0021738 A1 | 1/2007 | Hasser et al. | |
| 2009/0088774 A1* | 4/2009 | Swarup | A61B 34/37 |
| | | | 901/31 |
| 2009/0221958 A1 | 9/2009 | Beyar et al. | |
| 2010/0094312 A1 | 4/2010 | Ruiz Morales et al. | |
| 2010/0160728 A1 | 6/2010 | Yoshie | |
| 2013/0325029 A1 | 12/2013 | Hourtash et al. | |
| 2014/0018960 A1* | 1/2014 | Itkowitz | A61B 90/98 |
| | | | 700/264 |
| 2014/0142592 A1* | 5/2014 | Moon | A61B 34/37 |
| | | | 901/8 |
| 2014/0148819 A1 | 5/2014 | Inoue et al. | |
| 2014/0160015 A1* | 6/2014 | Ogawa | A61B 34/76 |
| | | | 345/156 |
| 2014/0165770 A1* | 6/2014 | Abri | B25J 13/025 |
| | | | 606/130 |
| 2014/0195052 A1 | 7/2014 | Tsusaka et al. | |
| 2015/0066051 A1* | 3/2015 | Kwon | A61B 34/76 |
| | | | 606/130 |
| 2016/0332305 A1* | 11/2016 | Gonzalez | B25J 13/025 |
| 2018/0243897 A1 | 8/2018 | Hashimoto et al. | |
| 2018/0250086 A1 | 9/2018 | Grubbs | |
| 2018/0310999 A1* | 11/2018 | Peine | B25J 11/008 |
| 2019/0008509 A1* | 1/2019 | Shelton, IV | A61B 17/07207 |
| 2019/0015169 A1* | 1/2019 | Verner | A61B 90/03 |
| 2019/0060019 A1 | 2/2019 | Maret | |
| 2019/0105117 A1 | 4/2019 | Brisson | |
| 2019/0184576 A1* | 6/2019 | Smith | B25J 13/087 |
| 2019/0231430 A1* | 8/2019 | Friman | A61B 90/36 |
| 2019/0328471 A1 | 10/2019 | Tojo et al. | |
| 2020/0022724 A1* | 1/2020 | Worrell | A61B 18/1442 |
| 2020/0222138 A1* | 7/2020 | Diolaiti | A61B 34/37 |
| 2020/0237461 A1* | 7/2020 | Kadokura | A61B 34/37 |
| 2020/0345433 A1* | 11/2020 | Peine | A61B 34/37 |
| 2021/0282795 A1 | 9/2021 | Shimono et al. | |

FOREIGN PATENT DOCUMENTS

| | | | | |
|---|---|---|---|---|
| EP | 2 739 441 B1 | 6/2014 | | |
| EP | 3342544 A1 * | 7/2018 | ........... | B25J 9/0087 |
| JP | 2010-507792 A | 3/2010 | | |
| JP | 4999012 B2 | 8/2012 | | |
| JP | 2013-035117 A | 2/2013 | | |
| JP | 2014-148037 A | 8/2014 | | |
| JP | 2017-512553 A | 5/2017 | | |
| JP | 2017-104914 A | 6/2017 | | |
| JP | 2019-187994 A | 10/2019 | | |
| WO | 2017/033379 A1 | 3/2017 | | |
| WO | 2017/098989 A1 | 6/2017 | | |
| WO | WO-2017220822 A1 * | 12/2017 | ........... | B25J 9/0084 |
| WO | 2019/017416 A1 | 1/2019 | | |
| WO | 2020/008807 A1 | 1/2020 | | |

OTHER PUBLICATIONS

Notice of Reasons for Refusal of Japanese Application No. 2020-021629 dated Jul. 28, 2020.

International Search Report of PCT/JP2021/000555 dated Mar. 23, 2021 [PCT/ISA/210].

International Preliminary Report on Patentability issued Aug. 11, 2022 in International Application No. PCT/JP2021/000555.

* cited by examiner

SURGICAL ROBOT AND CONTROLLER OF SURGICAL ROBOT

CROSS-REFERENCE TO RELATED APPLICATIONS

This U.S. application is a continuation application of International Application No. PCT/JP2021/000555, filed Jan. 8, 2021, which is based on and claims priority to Japanese Patent Application No. 2020-021629 filed on Feb. 12, 2020 with the Japan Patent Office, the contents of each of which being incorporated by reference herein in their entireties.

BACKGROUND

The present disclosure relates to a surgical robot suitable for use in endoscopic surgery and other surgeries.

A surgical robot is operated by a doctor or another medical worker and actuated to perform treatments, such as suturing, ablation, and excision, for tissue of a patient. In the surgical robot, in response to the user's operation, an operation signal is outputted from an operation part, and if a force required for the operation is too small, it may be difficult to perform the operation since the doctor or medical worker cannot obtain an intuitive feeling of operating a surgical robot. Hereinafter, the intuitive feeling of operating the surgical robot is also referred to as an "operational feeling". In addition, there may be a big difference between a treatment by one's own hand and a treatment using the surgical robot, making it difficult to operate the surgical robot. Also, if the force required for the operation is too small, the doctor or medical worker may move the surgical tool unnecessarily fast when performing an operation, and the doctor or medical worker may not be able to perform the operation well, and undesirable and unsafe conditions may occur, such as unintentional contact of the surgical tool with the tissue of the patient.

SUMMARY

It is an aspect to provide a surgical robot easy to operate with a desired operational feeling because a force required to the operation is suitably set.

According to an aspect of one or more embodiments, there is provided a surgical robot comprising an operation part that includes a movable part moved by a force applied by an operation by a user; an action part that performs an action according to the operation; a drive part that supplies a driving force to the action part; an operation controller that controls a movement of the movable part; and a controller configured to implement an operation force setter that sets a magnitude of a resistance force that is a force in a direction opposite to a direction of the movement of the movable part, wherein the operation force setter sets the magnitude of the resistance force based on a resistance parameter set in advance, and wherein the operation controller applies, to the movable part, the resistance force having the magnitude set by the operation force setter.

According to another aspect of one or more embodiments, there is provided a controller of a surgical robot that controls the surgical robot including an operation part having a movable part that is moved by an operation performed by a user, the controller comprising at least one microprocessor configured to set a magnitude of a resistance force that is a force in a direction opposite to a direction of the movement of the movable part; and control the movement of the movable part to apply, to the operation part, the resistance force having the magnitude, wherein the magnitude of the resistance force is set based on a resistance parameter set in advance.

According to yet another aspect of one or more embodiments, there is provided a surgical robot comprising an operation device that is movable to perform an operation by a force applied the operation device; a first actuator that controls a movement of the operation device in a first direction; and a controller configured to set a magnitude of a resistance force in a second direction opposite to the first direction, based on a resistance parameter that is set in advance, wherein the first actuator applies, to the operation device, the resistance force having the magnitude.

BRIEF DESCRIPTION OF THE DRAWINGS

The above and/or other aspects will become apparent and more readily appreciated from the following description of various embodiments, taken in conjunction with the accompanying drawings of which.

DETAILED DESCRIPTION

Figure 1:
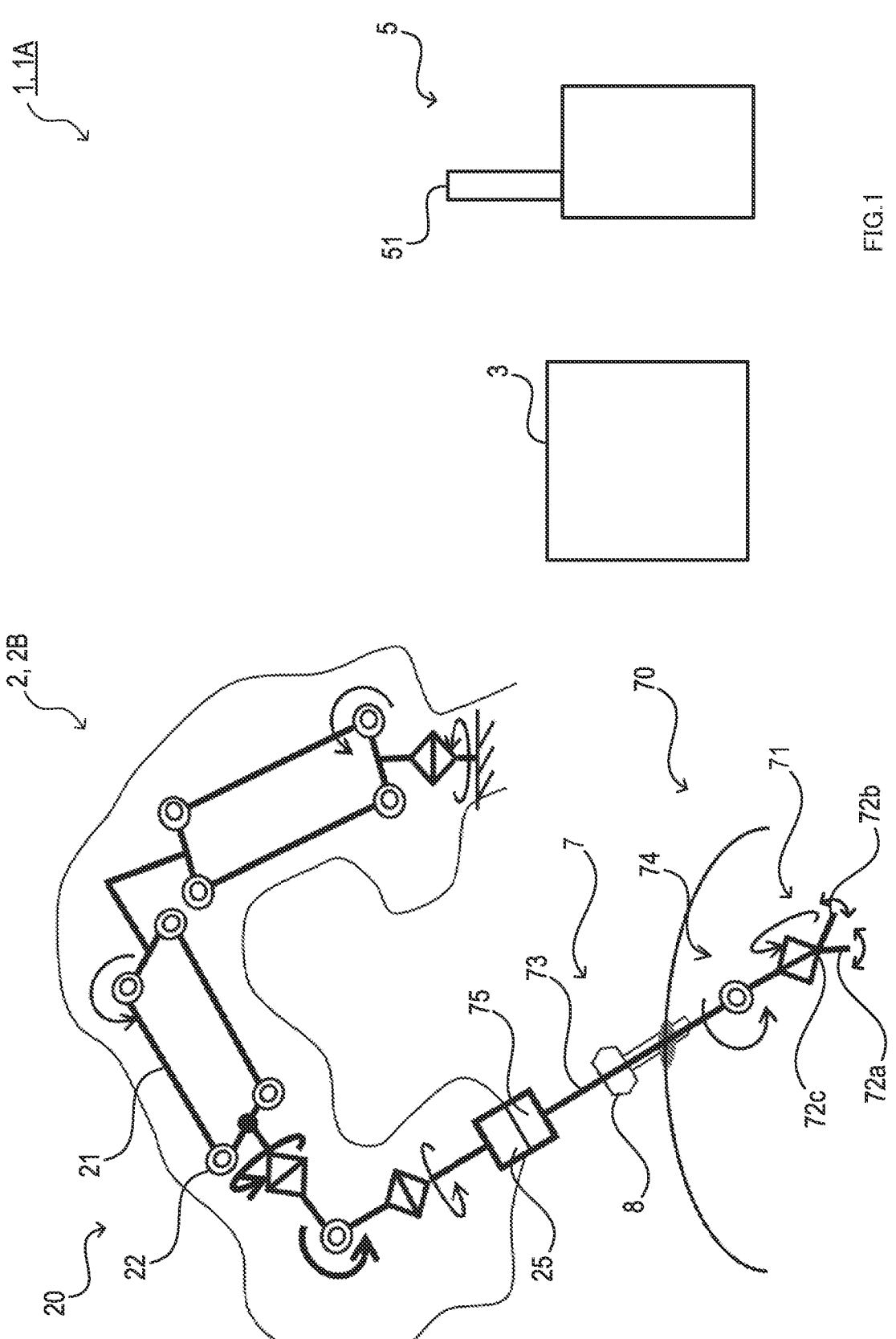
FIG. 1 is a view showing an appearance of a surgical robot according to some embodiments.

As discussed above, a surgical robot is operated by a doctor or another medical worker and actuated to perform treatments, such as suturing, ablation, and excision, for tissue of a patient. Hereinafter, the medical worker who operates the surgical robot is also referred to as "user". The surgical robot includes surgical instruments, such as forceps and electric scalpels to perform medical treatments. Hereinafter, the surgical instruments, such as forceps and electric scalpels to perform the medical treatments, are also referred to as "surgical tools". Furthermore, the surgical robot includes multiple arms supporting the surgical tools at desired positions and in desired postures. The arms and movable parts of the surgical tools are actuated according to the user's operation to perform the treatments for the tissue of the patient.

In the surgical robot described above, in response to the user's operation, an operation signal is outputted from an operation part, and the surgical robot performs an action according to the operation signal. That is, since the operation part is a part outputting the operation signal that is an electrical signal, the operation may be performed with a relatively small force.

However, if a force required for the operation is too small, it may be difficult to perform the operation since the user cannot obtain an intuitive feeling of operating a surgical robot. Hereinafter, the intuitive feeling of operating the surgical robot, which is a user's feeling during the operation, is also referred to as an "operational feeling". In addition, some users may find a big difference in feeling between a treatment by their own hand and a treatment using the surgical robot, making it difficult to operate the surgical robot. Also, if the force required for the operation is too small, the user may move the surgical tool unnecessarily fast when performing an operation, for example, to move the position of the surgical tool. In this case, the user may not be able to perform the operation well and undesirable and unsafe conditions may occur, such as unintentional and unsafe contact of the surgical tool with the tissue of the patient.

It is therefore an aspect of various embodiments to provide a surgical robot easy to operate with a desired operational feeling because a force required to the operation is suitably set.

A surgical robot according to one or more embodiments may include an operation part including a movable part moved by a force applied by an operation by a user; an action part performing an action according to the operation; a drive part supplying a driving force to the action part; an operation controller controlling a move of the movable part; and a resistance force setter setting a magnitude of a resistance force, the resistance force being a force inhibiting a movement of the movable part, the resistance force being a force in a direction opposite to a direction of movement of the movable part, wherein the resistance force setter sets a magnitude of the resistance force based on a resistance parameter set in advance, and wherein the operation controller applies, to the movable part, the resistance force having the magnitude set by the resistance force setter.

In the surgical robot configured in this way, when the user moves the movable part of the operation part to operate the surgical robot, a resistance force is applied to the movable part in a direction opposite to the operation direction, which is the direction of movement of the movable part. Therefore, the user operates the operation part while feeling the resistance force having the magnitude set in advance. This configuration allows the user to operate the operation part with a desired operational feeling.

The surgical robot may further include an input section receiving an input of information to set the resistance parameter, and the resistance force setter may set a magnitude of the resistance force based on the resistance parameter that is set based on information received by the input section.

In the surgical robot configured in this way, the user may set the resistance force of the operation part to a desired value. Therefore, it is possible to provide the surgical robot that the user may operate with an operational feeling matching the user's feeling more.

The action part of the surgical robot may be actuated to cause a specified portion of the surgical robot to move for a second distance corresponding to a first distance that is a distance of movement of the movable part, and the resistance force setter may set a magnitude of the resistance force based on the resistance parameter that is set based on a scaling coefficient that is a ratio of the first distance and the second distance.

In the surgical robot configured in this way, when the user moves the movable part for a specified distance, the resistance parameter is set by a scaling coefficient defining a distance in which a specified portion of the surgical robot moves. This scaling coefficient is defined according to the contents of the treatment provided by the surgical robot, a target site to be treated and others. That is, it is possible to provide the surgical robot that allows to set the resistance value depending on the contents of the treatment, the target site to be treated and others, and that the user may operate with a desired operational feeling.

The surgical robot may further include a reaction force setter setting a magnitude of an operation reaction force, the operation reaction force corresponding to the driving force, the operation reaction force being a force in a direction opposite to the direction of movement of the movable part, the reaction force setter setting the magnitude of the operation reaction force based on change information about a change in the driving force supplied by the drive part when the action part is actuated according to the operation, and the resistance force setter may set the magnitude of the resistance force based on the resistance parameter that is set based on the magnitude of the operation reaction force set by the reaction force setter, and the operation controller may apply, to the operation part, a force obtained by adding the resistance force having the magnitude set by the resistance force setter and the operation reaction force having the magnitude set by the reaction force setter.

In the surgical robot configured in this way, the resistance force is set based on the magnitude of the operation reaction force corresponding to the force applied by the activated surgical robot to the tissue to be treated. Therefore, it is possible to provide the surgical robot allowing the user to feel the desired operational feeling and to perceive the force applied to the tissue to be treated.

The surgical robot may further include an input section receiving input of user information about the user and a storage section storing the resistance parameter that is set for each user so as to be associated with the user information, and the resistance force setter may refer to the storage section and sets the magnitude of the resistance force based on the resistance parameter associated with the user information received by the input section.

In the surgical robot configured in this way, the desired resistance force may be set if the user simply enters the user's own information. Therefore, it is possible to provide the surgical robot that allows to easily set the resistance force suitable for the user.

The surgical robot may include multiple operation parts and multiple action parts corresponding to the multiple operation parts, and the resistance force setter may set a magnitude of the resistance force for each of the multiple operation parts.

In the surgical robot configured in this way, it is possible to set a suitable resistance force to each of the multiple operation parts depending on the contents of the treatment, the target site to be treated and others. Therefore, it is possible to provide the surgical robot that the user may operate with the user's desired feeling of use depending on the contents of the treatment, the target site to be treated and others.

The surgical robot according to various embodiments provides a surgical robot that a user may operate with a desired operational feeling when operating the surgical robot.

Embodiments described below are examples of embodiments that fall within the technical scope of this disclosure. That is, the technical scope of the present disclosure is not limited to the specific configurations, structures, and others shown in the embodiments described below.

Directional arrows, oblique lines, and others in each figure are described to facilitate understanding of the relationship between the figures, and the shape of each member or part. Therefore, the technical scope of the present disclosure is not limited to the directions described in each figure. The figures with the oblique lines do not necessarily show sectional views.

At least one member or one part is provided for a member or a part at least described with a reference numeral, except when the member or the part is explicitly described as "one member" or the like. In other words, if there is no mention of "one member" or the like, two or more of such members may be provided. The surgical robot of the present disclosure includes components, such as members and parts at least described with reference numerals, and illustrated structural parts.

Hereinafter, a surgical robot according to some embodiments will be described with reference to FIG. 1 to FIG. 6. A description will be made of an example embodiment in which the surgical robot is used for endoscopic surgery. In the following description, directions of front-back, left-right, and up-down are directions shown in the figures unless otherwise specified.

<1. Description of Configuration>

As shown in FIG. 1, a surgical robot 1 may include a robot arm 2, a controller 3, an operation unit 5 and a surgical tool 7. The surgical tool 7 is supported by the robot arm 2.

In some embodiments, the surgical robot 1 may include one robot arm 2. In other embodiments, the surgical robot 1 may include multiple robot arms 2. In some embodiments, the surgical robot 1 may have a configuration having multiple surgical tools 7 supported by the multiple robot arms 2.

<Surgical Tool>

First, the surgical tool 7 will be described. The surgical tool 7 is an instrument a part of which is inserted into a body of a targeted person through a trocar 8 perforating in the abdomen or another part of the targeted person undergoing the surgery, thereby performing a treatment for tissue. Hereinafter, the targeted person undergoing the surgery is also referred to as "patient". In some embodiments, a description will be made of an example in which the surgical tool 7 is a pair of forceps used in endoscopic surgeries.

The surgical tool 7 may include a grasper 71, a shaft 73 and an adapter 75. The grasper 71 is a part inserted into the patient's body through the trocar 8 to perform a treatment such as grasping of tissue or the like, and the grasper 71 is provided on an end side of the shaft 73. Hereinafter, the side of the shaft 73 where the grasper 71 is provided is also referred to as "tip side" of the shaft 73 or "tip side" of the surgical tool 7.

The shaft 73 is an elongated cylindrical part having the adapter 75 on the opposite side of the grasper 71. The shaft 73 includes a wrist 74 in an area near the grasper 71, and the wrist 74 may be folded in a specified direction or bent in a specified direction around a specified axis. The wrist 74 is a part to change the orientation of the grasper 71 by being folded or bent in a specified direction.

The grasper 71 may include a jaw 72a, a jaw 72b corresponding to the jaw 72a, and a base 72c. The jaw 72a and the jaw 72b are supported by the base 72c so as to be movable closer together and apart from each other.

By the jaw 72a and the jaw 72b moving closer together, the grasper 71 performs an action of grasping the tissue or the like located between the jaw 72a and the jaw 72b. By the jaw 72a and the jaw 72b moving apart from each other, the grasper 71 performs an action of releasing the grasped tissue or the like. Hereinafter, moving the jaw 72a and the jaw 72b closer together is also described as "closing" the grasper 71, and moving the jaw 72a and the jaw 72b apart from each other is also described as "opening" the grasper 71. The action of opening and closing the grasper 71 is also referred to as "open/close action".

Inside the cylindrical shaft 73, unillustrated wires are provided to cause the grasper 71 and the wrist 74 to perform specified actions. In response to a specified tension being applied to the wires, a corresponding part of the grasper 71 or the wrist 74 performs an action according to the tension. Hereinafter, the grasper 71, the wrist 74, and other parts of the surgical tool 7, which are actuated when the specified tension or the like is applied to the wires, are also collectively referred to as "action part of the surgical tool 7" or "action part 70".

<Robot Arm>

The robot arm 2 may be an arm device actuated according to the user's operation to hold the surgical tool 7 in a posture and at a position according to the operation. In other words, the robot arm 2 holds the surgical tool 7 so that a tip portion of the surgical tool 7 is held at a position and in a posture desired by the user. In some embodiments, the grasper 71 is the tip portion of the surgical tool 7.

That is, in response to the user's operation, the robot arm 2 is actuated so that the tip portion of the surgical tool 7, i.e. the grasper 71 is moved in a direction according to the operation. Hereinafter, the direction in which the tip portion of the surgical tool 7 is moved according to the user's operation is also referred to as "direction of movement of the surgical tool 7", or simply referred to as "direction of movement".

The robot arm 2 may include a link mechanism including multiple joint parts 22. That is, the robot arm 2 may include multiple arms 21 connected to the joint parts 22 so that the multiple arms 21 are rotatable in specified directions.

The robot arm 2 includes a connector 25 detachably connecting the surgical tool 7. The adapter 75 of the surgical tool 7 is connected to this connector 25, whereby the surgical tool 7 is supported by the robot arm 2.

Figure 2:
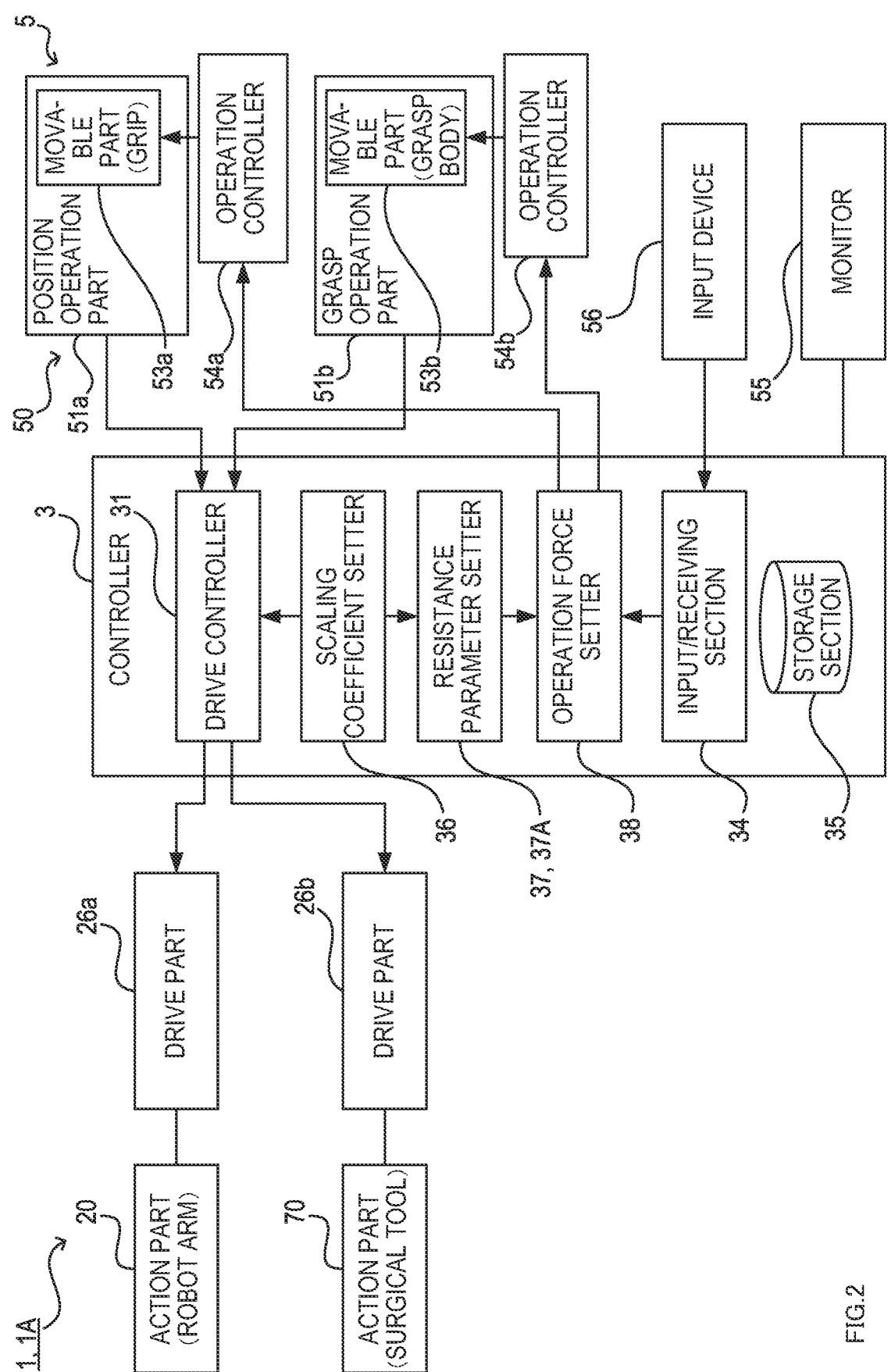
FIG. 2 is a block diagram of the surgical robot according to some embodiments.

As shown in FIG. 2, the robot arm 2 includes multiple drive parts 26a to cause the arms 21 and/or joints 22 to perform actions according to the user's operation. The drive part 26a is a part performing physical movement in response to the user's operation to provide a specified driving force to the arm 21 and/or the joint part 22. In FIG. 2, one drive part 26a is described as an example and the descriptions of other drive parts 26a are omitted for conciseness.

In response to the user performing a specified operation with the operation unit 5, the drive part 26a corresponding to the operation is actuated to apply a driving force, which has a magnitude corresponding to the operation, to the corresponding arm 21 and/or the joint part 22. Then, the corresponding arm 21 is rotated around the joint part 22 or moved in a direction according to the user's operation. When the arm 21 and the joint part 22 are actuated in this way, the robot arm 2 is actuated according to the user's operation. Hereinafter, the arm 21 and the joint 22 that are actuated by the driving force from the drive part 26a are also collectively referred to as "action part of the robot arm 2" or "action part 20". In FIG. 2, for explanation purposes, the arm 21 and the joint part 22 corresponding to one drive part 26a are collectively described as an action part 20, and the descriptions of other arms 21 and joint parts 22 are omitted.

The robot arm 2 also includes multiple drive parts 26b applying forces to cause the grasper 71, the wrist 74, and/or other parts of the surgical tool 7 to perform specified actions. This drive part 26b is a part performing physical movement according to the user's operation to apply a driving force to a specified part of the adapter 75 of the surgical tool 7 to cause the grasper 71 and/or other parts to perform actions according to the user's operation. In FIG. 2, for explanation purposes, one drive part 26b is described as an example and the descriptions of other drive parts 26a are omitted.

In some embodiments, the following description will be made of an example of a configuration in which the drive part 26a and drive part 26b each include a pneumatic actuator. That is, in some embodiments, the drive part 26a and the drive part 26b are each configured of a pneumatic cylinder, a pressure generator that supplies compressed air to the pneumatic cylinder, and a control electromagnetic valve. The drive part 26a and the drive part 26b are each configured of a force transmission mechanism or another mechanism that transmits the movement of the pneumatic cylinder to a specified part. The above-described configurations of the drive part 26a and the drive part 26b are examples, and embodiments are not limited to the above-described configurations. Hereinafter, the drive parts 26a, 26b are also collectively referred to as "drive part 26".

<Operation Unit>

As shown in FIG. 2, the operation unit 5 may be a part with which the user performs operations, and includes a monitor 55, an operation device 50, and an input device 56. In the case where the surgical robot 1 includes multiple robot arms 2, the operation unit 5 may include multiple operation devices 50 respectively corresponding to the multiple robot arms 2.

The monitor 55 may display a setting screen for the settings necessary for the operation, an endoscope image of the patient, the states of the robot arm 2 and the surgical tool 7, and/or indications used for the operation of the robot arm 2 and the surgical tool 7. The endoscope image is an image inside the body cavity of the patient, and the image is obtained by an unillustrated endoscope inserted into the body cavity of the patient through an unillustrated another trocar puncturing the abdomen or another part of the patient. The endoscope is held by another robot arm, another endoscope holder, or an endoscope holding apparatus. The above-described other robot arm, the endoscope holder, and the endoscope holding apparatus are not illustrated in FIG. 1 to FIG. 6.

The input device 56 may be, for example, a keyboard, a mouse, a touch panel, a foot switch, or the like.

The operation device 50 may be a device with which the user operates the robot arm 2 and the surgical tool 7. In other words, the operation device 50 is a part outputting an operation signal to cause the robot arm 2 and the first surgical tool 7 to perform actions according to the user's operation.

Figures 3A, 3B:
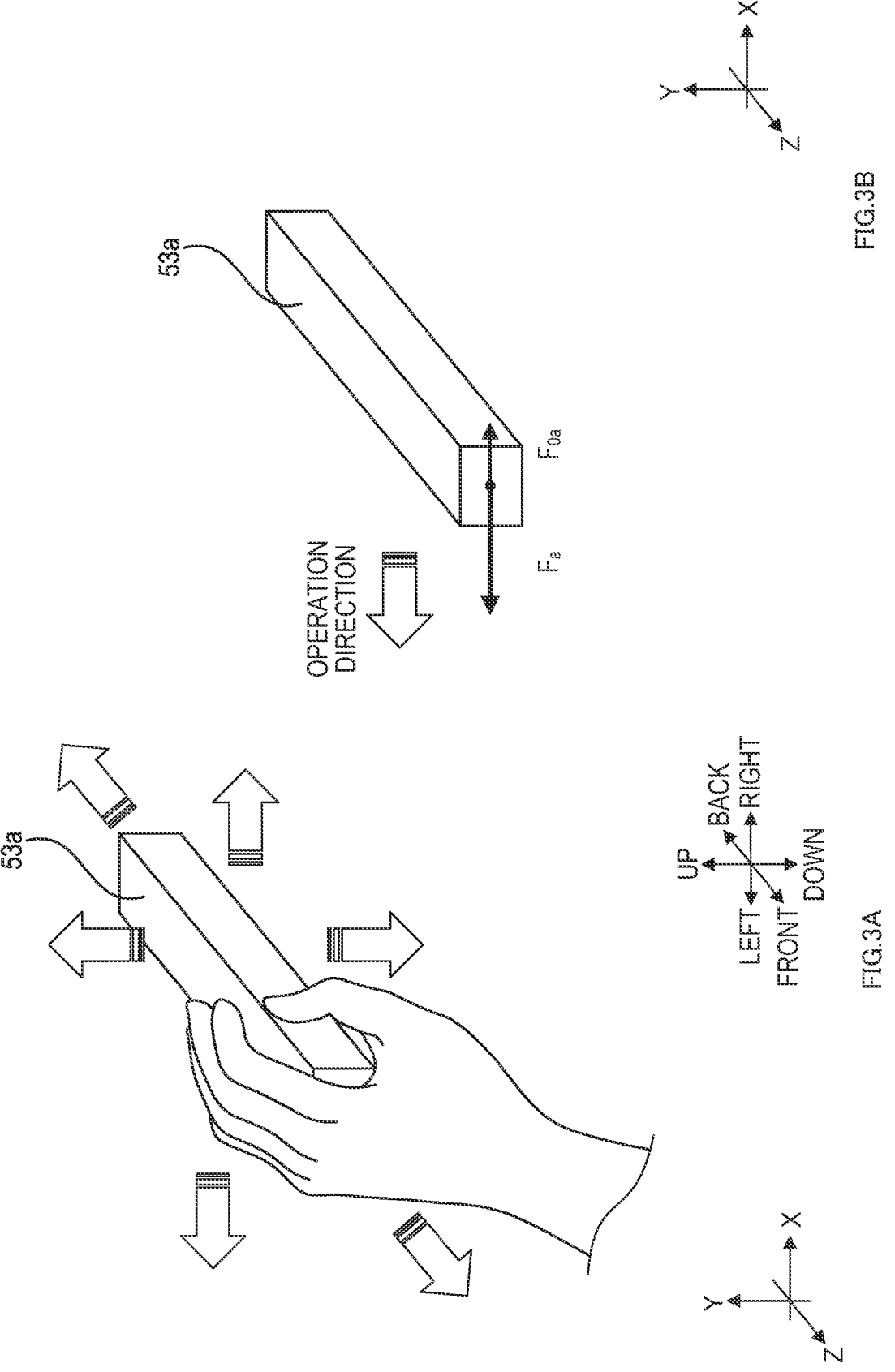
FIGS. 3A and 3B are schematic views showing examples of an operation part of the surgical robot according to some embodiments.

FIGS. 3A and 3B are schematic views showing examples of an operation part of the surgical robot according to some embodiments. The operation device 50 includes the position operation part 51a and the grasp operation part 51b. The position operation part 51a may be a part operated by the user to change the position of the tip side of the surgical tool 7, or more specifically, the position of the grasper 71. That is, in response to the position operation part 51a being operated, the robot arm 2 is controlled so that the grasper 71 moves in a direction according to the user's operation.

The grasp operation part 51b may be a part operated by the user to cause the grasper 71 of the surgical tool 7 to perform an open/close action. That is, in response to the grasp operation part 51b being operated, the robot arm 2 is controlled to cause the grasper 71 to perform the open/close action according to the user's operation. The position operation part 51a or the grasp operation part 51b may be used to operate another part such as the wrist 74 of the surgical tool 7 by a switching operation of an input device 56 such as a foot switch.

In some embodiments, the position operation part 51a may be an operation device configured of a grip 53a supported by an unillustrated support part. The grip 53a is a part that is held by the user during the operation and that is moved in desired directions. As shown in FIG. 3A, the grip 53a is supported by a support part so as to be movable in an up-down direction, a front-rear direction, and a left-right direction, i.e. in an arbitrary three-dimensional direction. Thus, the user may hold the grip 53a and move the grip 53a in the arbitrary three-dimensional direction within a specified range. In some embodiments, with respect to directions in which the grip 53a moves, the up-down direction is referred to as "Y-direction", the left-right direction is referred to as "X-direction", and the front-rear direction is referred to as "Z-direction". In some embodiments, the up-down direction in which the grip 53a moves is also referred to as "Y-axis direction", the left-right direction is also referred to as "X-axis direction", and the front-rear direction is also referred to as "Z-axis direction". The shape of the grip 53a shown in FIG. 3A and FIG. 3B is an example and the shape is not limited to the illustrated shape.

In some embodiments, the grip 53a may be movably supported in the arbitrary three-dimensional direction by the support part configured of a link mechanism. For the position operation part 51a, an operation device having another configuration may be used as long as the device has a part movable in the arbitrary direction and the device is suitable for the operation of the robot arm 2.

Figure 4B:
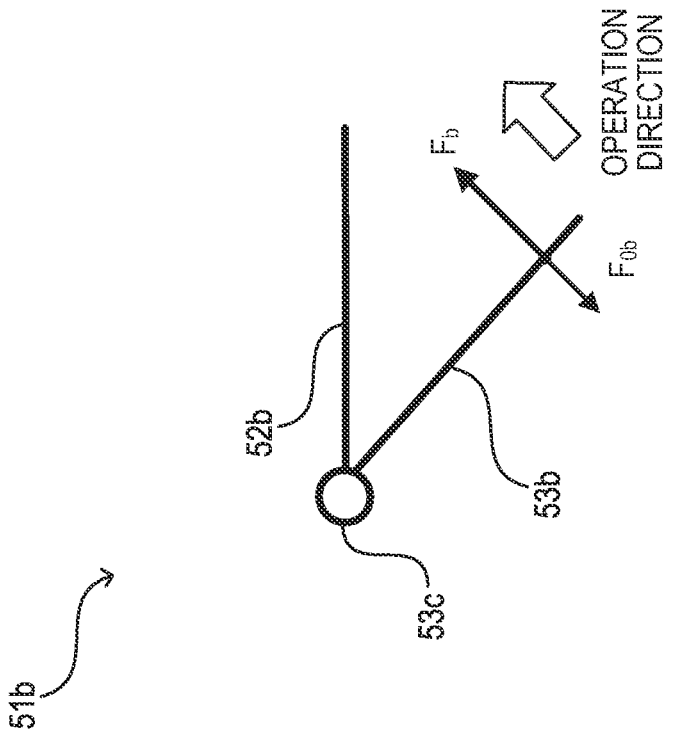
FIGS. 4A and 4B are schematic views showing examples of an operation part of the surgical robot according to some embodiments.
Figure 4B:
Figure 4A:
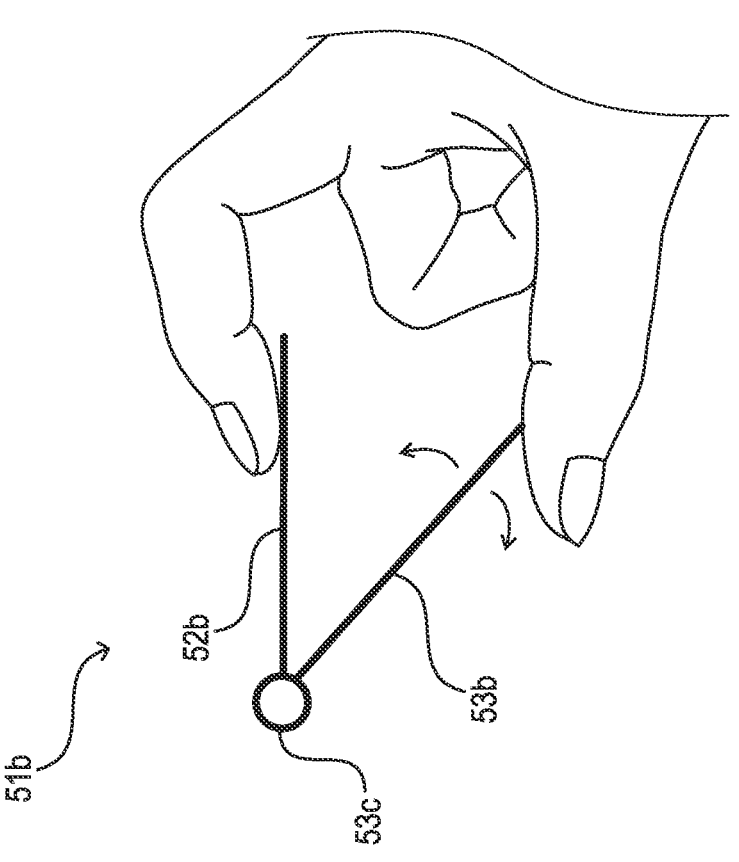

FIGS. 4A and 4B are schematic views showing examples of an operation part of the surgical robot according to some embodiments. As shown in FIG. 4A and FIG. 4B, the grasp operation part 51b of some embodiments is an operation device including a grasp body 53b and a support body 52b rotatably supporting the grasp body 53b. The grasp body 53b is supported, at a joint 53c provided to the support body 52b, so as to be rotatable relative to the support body 52b. The shape of the grasp operation part 51b shown in FIG. 4A and FIG. 4B is an example and the shape is not limited to the illustrated shape.

As shown in FIG. 4A, the grasp operation part 51b is held so that the grasp body 53b and the support body 52b are held between fingers, such as the thumb and the index finger, of the user to perform the operation of moving the grasp body 53b closer to and away from the support body 52b. For the grasp operation part 51b, an operation device having another configuration may be used as long as the device has a part movable in a specified direction and the device is suitable for the operation of the grasper 71.

In some embodiments, the grasp operation part 51b is provided in an area on a support part 52a side of the grip 53a, that is, in an area in which the user's fingers are placed when the user holds the grip 53a. The grasp operation part 51b may be provided in an area different from the above-described area as long as the user may operate the grasp operation part 51b.

Hereinafter, the position operation part 51a and the grasp operation part 51b are also collectively referred to as "operation part 51". The directions in which the grip 53a and the grasp body 53b are moved by the user's operation are also referred to as "operation direction of the operation part 51", or simply referred to as "operation direction". The grip 53a and the grasp body 53b are also collectively referred to as "movable part 53".

The position operation part 51a is provided with unillustrated multiple sensors, such as encoders, to detect the position of the grip 53a. That is, when the grip 53a is moved by the user's operation, the position operation part 51a outputs operation signals corresponding to a direction of movement and a distance of movement of the grip 53a to the drive controller 31 described below in detail.

The grasp operation part 51b is also provided with a sensor, such as an encoder, to detect an angle, a distance, or the like between the support body 52b and the grasp body 53b. Thus, when the user operates the grasp operation part 51b and changes the position of the grasp body 53b, the grasp operation part 51b outputs an operation signal corresponding to the movement of the grasp body 53b to the drive controller 31 described below in detail.

The operation device 50 further includes operation controllers 54a, 54b controlling the movement of the grip 53a and the grasp body 53b. The operation controllers 54a, 54b are parts respectively applying forces having magnitudes set by the reaction force setter 38 described below in detail to the position operation part 51a and the grasp operation part 51b, thereby controlling the forces required to move the grip 53a and the grasp body 53b.

Specifically, the operation controller 54a includes an actuator outputting a force having a magnitude based on a signal from the operation force setter 38. The operation controller 54a also includes a force transmission mechanism to apply the force outputted from the actuator to the grip 53a in a direction opposite to the operation direction of the position operation part 51a.

Similarly, the operation controller 54b includes an actuator outputting a force having a magnitude based on a signal from the operation force setter 38. The operation controller 54b also includes a force transmission mechanism to apply the force outputted from the actuator to the grasp body 53b in a direction opposite to the operation direction of the grasp operation part 51b.

In some embodiments, a description will be made of an example in which the operation controllers 54a, 54b each include a force transmission mechanism configured of a pneumatic actuator, a link, a wire, a pulley and/or other elements. The operation controllers 54a, 54b may each have a configuration in which an electric actuator, an electric motor, and/or another actuator is provided as the actuator. The operation controllers 54a, 54b may be each provided with a force transmission mechanism configured of a link mechanism or another mechanism. Hereinafter, the operation controller 54a and the operation controller 54b are also collectively referred to as "operation controller 54".

<Operation Force>

Here, a description will be made of "operation force" that is a force applied to the operation part 51 when the user performs an operation using the operation device 50.

When the user operates the operation part 51, the user applies a force having a certain magnitude to the movable part 53 and changes the position of the movable part 53. That is, the user operates operation part 51 by moving the movable part 53. Here, "operation force" means a force that the user applies to the movable part 53 for the operation.

Here, in a state that the surgical tool 7 is not in contact with the tissue or the like of the patient and no external force is applied, the operation force required of the user to move the movable part is referred to as "operation force during movement". For example, the operation force during movement may be a threshold force.

When the user applies a force F equal to or larger than the operation force during movement $F_0$ to the movable part 53, the movable part 53 is moved in the direction of the force applied by the user, and the corresponding action parts 20, 70 are actuated. On the other hand, when the force applied to the movable part 53 is less than the operation force during movement $F_0$, the movable part 53 is not moved and the action parts 20, 70 are not actuated.

That is, to the movable part 53, a force having a magnitude equal to the operation force during movement but in the opposite direction is applied. It may also be said that the magnitude of the operation force during movement is determined by the force in the opposite direction. Hereinafter, the force having the magnitude equal to the operation force during movement but in the opposite direction is referred to as "resistance force".

Therefore, if the resistance force is small, the user may operate the operation part 51 just by applying a force having a small magnitude to the movable part 53. If the resistance force is large, the user needs to apply a force having a relatively large magnitude to the movable part 53 in order to operate the operation part 51.

In general, the resistance force is felt differently by different users. In other words, if the resistance force is small, some users may feel that the movable part 53 is moved so easily that the operation is difficult and may find that the operational feeling of the movable part 53 is too light. On the other hand, other users may feel that if the resistance force is small, the operation is easier because the operation may be performed with a small force. In some cases, some users may feel the large resistance force is more suitable for the operation because a careful operation may be performed. On the other hand, other users may feel that the operation is difficult because a superfluous force needs to be applied to the movable part 53, and may find that the operational feeling of the movable part 53 is too heavy.

Therefore, the surgical robot 1 according to various embodiments has a function of causing the operation controller 54 to apply a force having a magnitude according to the user's settings to the movable part 53, thereby controlling the resistance force $F_0$ of the operation part 51.

<Controller>

As shown in FIG. 2, a controller 3 may be a part performing the control of the robot arm 2 and the operation unit 5. The controller 3 includes a drive controller 31, a scaling coefficient setter 36, a resistance parameter setter 37, an operation force setter 38, an input/receiving section 34, and a storage section 35.

In some embodiments, the controller 3 is a computer system that includes hardware control logic, one or more microprocessors or one or more microcontrollers and has specialized software installed. That is, the specialized software and hardware (e.g., the hardware control logic, microprocessor, or microcontroller) cooperate to fulfill a function of each section, such as the drive controller 31, the scaling coefficient setter 36, the resistance parameter setter 37, the operation force setter 38, the input/receiving section 34, and the storage section 35. In the controller 3, each section described below in detail may be configured of specialized hardware fulfilling its function.

The drive controller 31 may be a part controlling the drive part 26 according to an operation signal outputted from the operation unit 5 in response to the user's operation. That is, the drive controller 31 is a part that controls the corresponding drive parts 26a, 26b to output the driving forces according to the inputted operation signals so that the robot arm 2 and the surgical tool 7 perform actions according to the user's operations of the position operation part 51a and the grasp operation part 51b.

The scaling coefficient setter 36 is a part that sets a scaling coefficient, which is a ratio between a distance in which the movable part 53 is moved by the user's operation and a distance in which the tip portion of the surgical tool 7, i.e. the grasper 71 is moved by the operation. Hereinafter, the distance in which the movable part 53 is moved by the user's operation is also referred to as "distance of movement of the operation part". The distance in which the tip portion of the surgical tool 7 is moved is also referred to as "distance of movement of the surgical tool".

For the purpose of providing a specific explanation, a description will be made of an example in which, if the scaling coefficient is set to "1" and the movable part 53 is moved by a distance "$L_1$", the tip portion of the surgical tool 7 is set to move by a distance "$L_2$". In this case, when the scaling coefficient is set to "0.5" and the user moves the grip 53$a$ by a distance "$L_1$", the corresponding part of the tip side of the surgical tool 7 is controlled to move by a distance "$L_2 \times 0.5$". At that time, the corresponding part of the tip side of the surgical tool 7 is moved in a direction corresponding to the direction of movement of the grip 53$a$.

For example, when the scaling coefficient is set to "1.2" and the user moves the grip 53$b$ by a distance "$L_1$", the corresponding part of the grasper 71 is controlled to move by a distance "$L_2 \times 1.2$". At this time, the corresponding part of the grasper 71 is moved in a direction corresponding to the direction of movement of the grasp body 53$b$.

That is, if the scaling coefficient is set to a small value, the distance of movement of the surgical tool relative to the distance of movement of the operation part becomes short, making it easier to perform a minute treatment, for example. On the other hand, if the scaling coefficient is set to a large value, the distance of movement of the surgical tool relative to the distance of movement of the operation part becomes long, enabling faster movement of the surgical tool 7. That is, the scaling coefficient is a coefficient that is set depending on the contents, purpose or the like of the treatment provided using the surgical tool 7, and the scaling coefficient setter 36 is a part causing the drive controller 31 to perform control according to the set scaling coefficient.

The resistance parameter setter 37 may be a part that sets a resistance parameter, which is used when the operation force setter 38 described below in detail sets a resistance force outputted by the operation controller 54.

The operation force setter 38 may be a part that sets a resistance force based on the resistance parameter set by the resistance parameter setter 37 and that outputs a signal to cause the operation controller 54 to output a force having the set magnitude. The operation force setter 38 is one example of a resistance force setter.

The input/receiving section 34 may be a part receiving information inputted by the user using an input device 56, and also serving as an interface with the input device 56. The input/receiving section 34 receives information about the resistance parameter inputted by the user. The input/receiving section 34 also receives input of information related to the contents of the surgery performed by the surgical robot 1 such as information about the user, the contents of the treatment and the patient, and other information. The input/receiving section 34 is one example of an input section.

The storage section 35 may be a storage medium, such as a hard disk or a memory, and may store a program necessary for a process by the controller 3 and storing information related to the settings necessary for the operation of the surgical robot 1. The storage section 35 may store other information about the surgical robot 1.

<2. Details of Control>

Figure 5:
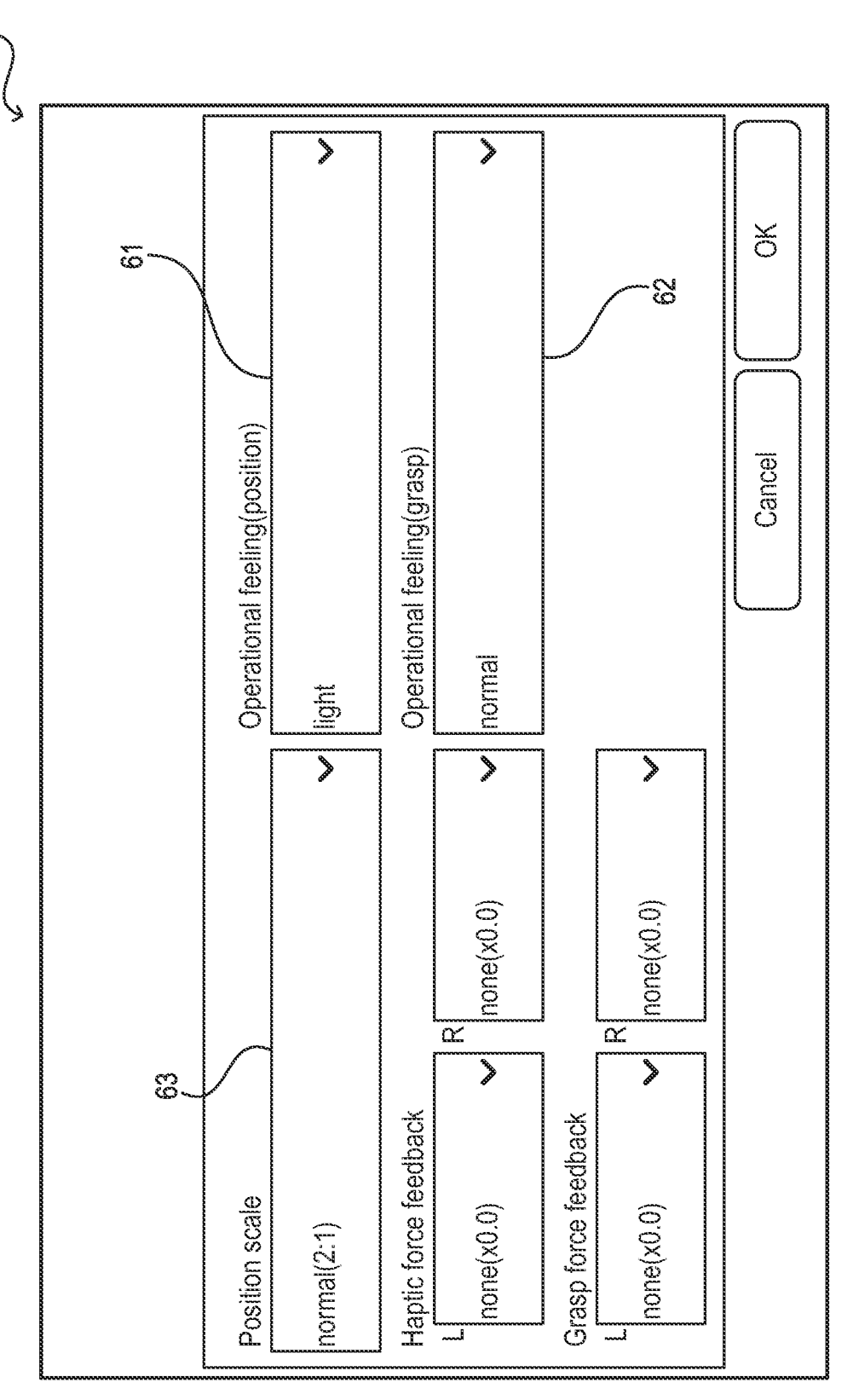
FIG. 5 is a view showing an example of a setting screen of the surgical robot according to some embodiments.
Figure 6:
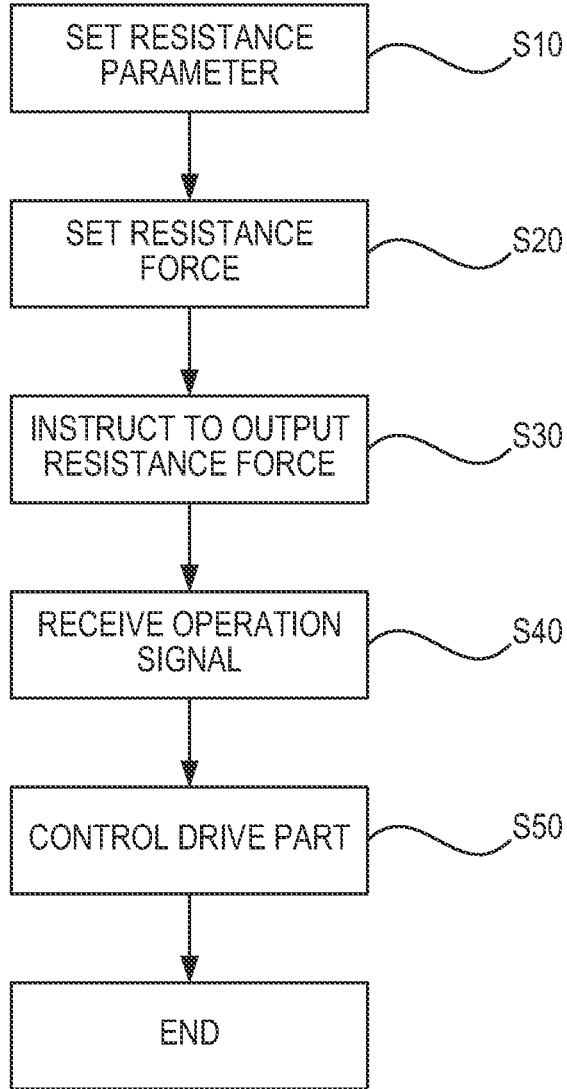
FIG. 6 is a flow diagram showing an example of a process flow by the surgical robot according to some embodiments.

FIG. 5 is a view showing an example of a setting screen of the surgical robot according to some embodiments, and FIG. 6 is a flow diagram showing an example of a process flow by the surgical robot according to some embodiments.

With reference to FIG. 5 and FIG. 6, the control of the surgical robot 1 will be described along a method for operating the surgical robot.

In response to the surgical robot 1 being powered on and a specified operation is performed, the surgical robot 1 starts up. The input/receiving section 34 receives information, such as user information about the user, information about a patient, and information about a site to be treated, which are inputted by the user according to a specified screen displayed on the monitor 55.

Then, in response to the user further performing a specified operation, a setting screen 60 as shown in FIG. 5 is displayed on the monitor 55. The setting screen 60 is provided with a movement resistance parameter input field 61, a grasp resistance parameter input field 62, and a scaling coefficient input field 63. The movement resistance parameter input field 61 is a field in which information to set a resistance parameter related to the operation force during movement at the time of operating the position operation part 51$a$ is inputted. The grasp resistance parameter input field 62 is a field in which information to set a resistance parameter related to the operation force during movement at the time of operating the grasp operation part 51$b$ is inputted. The scaling coefficient input field 63 is a field in which information to set the scaling coefficient is inputted. Hereinafter, the operation force during movement at the time of operating the position operation part 51$a$ and/or the grasp operation part 51$b$ is also referred to as "resistance force".

In response to the user operating the input device 56 and inputting information to set desired resistance parameters into the movement resistance parameter input field 61 and the grasp resistance parameter input field 62, the input/receiving section 34 receives the information.

In some embodiments, the user may input the information by selecting the desired settings from multiple options displayed in each of the movement resistance parameter input field 61 and the grasp resistance parameter input field 62. The user may also input the resistance parameters by directly entering numeral values or the like related to the settings of the resistance parameters.

The resistance parameter setter 37 sets each resistance parameter based on the information received by the input/receiving section 34 (S10).

In response to the user operating the input device 56 and inputting information to set a desired scaling coefficient into the scaling coefficient input field 63, the input/receiving section 34 receives the information. In some embodiments, the user may input the information by selecting a desired setting from multiple options displayed in the scaling coefficient input field 63. In some embodiments, the user may also input the information by directly entering a numeral value or the like related to the setting of the scaling coefficient. The scaling coefficient setter 36 sets the scaling coefficient based on the information received by the input/receiving section 34.

The operation force setter 38 sets the magnitudes of the operation forces during movement based on the resistance parameters set by the resistance parameter setter 37 (S20). In some embodiments, a description will be made of, as an example, a case where the operation force setter 38 sets $F_{0a}$ as the resistance force applied to the position operation part $51a$ and sets $F_{Ob}$ as the resistance force applied to the grasp operation part $51b$.

The operation force setter 38 outputs signals to the operation controllers 54a, 54b to cause them to output the set resistance forces (S30). Specifically, the operation force setter 38 outputs a signal to the operation controller 54a to cause the operation controller 54a to output the resistance force $F_{Oa}$ in the direction opposite to the operation direction of the grip 53a as shown in FIG. 3B. The operation force setter 38 also outputs a signal to the operation controller 54b to cause the operation controller 54b to output the resistance force $F_{Ob}$ in the direction opposite to the operation direction of the grasp body 53b as shown in FIG. 4B.

In response to the user operating the position operation part 51a and the grasp operation part 51b, the position operation part 51a and the grasp operation part 51b output operation signals according to the operation to the drive controller 31. For example, the user applies a force $F_a$ larger than the force $F_{Oa}$ to the grip 53a to operate the grip 53a. The user also applies a force $F_b$ larger than the force $F_{Ob}$ to the grasp body 53b to operate the grasp body 53b.

In response to the operation signal being inputted (S40), the drive controller 31 actuates the corresponding drive part 26 based on the inputted operation signal and the scaling coefficient set in the scaling coefficient input field 63. That is, the corresponding drive part 26 is controlled so that the action part 20 and the action part 70 are actuated according to the user's operation (S50). After an intended treatment is performed and the surgery is completed, the process is terminated according to a specified operation by the user.

In the surgical robot 1 according to some embodiments, when the user moves the movable part 53 of the operation part 51 to operate the moveable part 53, the resistance force is applied to the movable part 53 in the direction opposite to the direction of movement, i.e. the operation direction of the movable part 53. Therefore, the user may operate the operation part 51 while feeling the resistance force having a magnitude set in advance. That is, the user may operate the surgical robot with the user's desired operational feeling, and thus, the surgical robot is easy to operate.

The user may input the desired resistance parameters into the movement resistance parameter input field 61 and the grasp resistance parameter input field 62, and thus, the user may change the resistance forces to the desired values. This configuration makes it possible to provide a surgical robot that provides the user with an operational feeling matching the user's feeling more and that is easy to operate.

Moreover, the movement resistance parameter input field 61 and the grasp resistance parameter input field 62 are provided independently. Therefore, each of the resistance force of the position operation part 51a and the resistance force of the grasp operation part 51b may be set individually. Therefore, various settings may be made depending on the user's preference and the treatment to be performed. For example, with respect to the movement of the grip 53a, the resistance force may be increased to provide a heavy operational feeling, while with respect to the movement of the grasp body 53b, the resistance force may be decreased to provide a light operational feeling. In some embodiments, with respect to the movement of grip 53a, the resistance force may be decreased to provide a light operational feeling, while with respect to the movement of the grasp body 53b, the resistance force may be increased to provide a heavy operational feeling. In some embodiments, with respect to the movements of the grip 53a and the grasp body 53b, the resistance forces may be decreased to provide light operational feelings. In some embodiments, with respect to the movements of the grip 53a and the grasp body 53b, the resistance forces may be increased to provide heavy operational feelings. That is, various settings matching the user's preference and the purpose of use may be made. Therefore, it is possible to provide a surgical robot that matches the user's operational feeling more and that is easy to operate.

The resistance parameter related to the position operation part 51a and the resistance parameter related to the grasp operation part 51b may be set in advance for each user and may be stored in the storage section 35 together with the user information about the user. That is, the resistance parameters related to the position actuator 51a and the grasp actuator 51b, which are set in advance for each user, may be associated with the user information and stored in the storage section 35. The resistance parameter setter 37 may be configured to refer to the storage section 35 based on the user information about the user received by the input/receiving section 34 to set the resistance parameters associated with the user information. In this way, simply by entering the user's own user information at the start of use, for example, the desired resistance parameters may be set, thus making the surgical robot easy to set up.

For each site to be treated or for each type of procedure or the like, suitable resistance parameters may be set in advance, and the combination thereof may be stored in the storage section 35. The resistance parameter setter 37 may be configured to refer to the storage section 35 based on the information or the like about the site to be treated and/or the information about the type of procedure received by the input/receiving section 34 to set the resistance parameters associated with such information. With this configuration, for example, simply by entering the information about the site or the like to be treated by the surgical robot 1 at the start of use, the resistance parameters suitable for the site are set, thereby making the surgical robot easy to set up.

Figure 7:
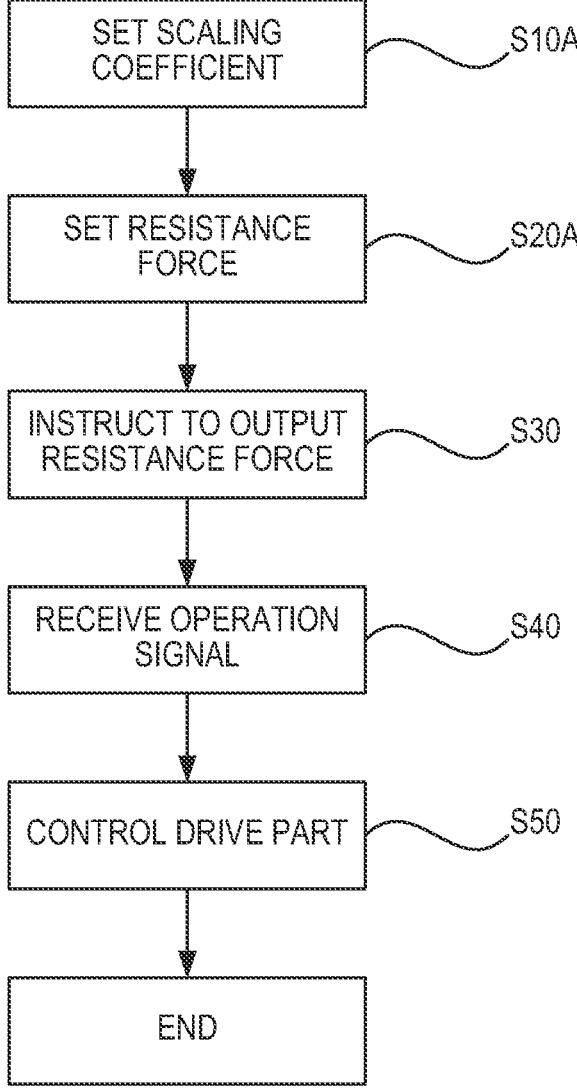
FIG. 7 is a flow diagram showing an example of a process flow by a surgical robot according to some embodiments.

FIG. 7 is a flow diagram showing an example of a process flow by a surgical robot according to some embodiments.

Hereinafter, embodiment process flow by the surgical robot will be described with reference to FIG. 7.

The process flow may be performed, for example, by the surgical robot 1A according to some embodiments. However, a process to set the resistance parameters is different from the process flow illustrated in FIG. 6.

Thus, differences will be described with reference to FIG. 7, and the parts same as those illustrated in FIG. 6 will be denoted by the same reference numerals, and the descriptions thereof will be omitted for conciseness.

A resistance parameter setter 37A of the surgical robot 1A according to some embodiments sets the resistance parameter based on the scaling coefficient set by the scaling coefficient setter 36.

Specifically, in response to the scaling coefficient setter 36 setting a scaling coefficient according to the input by the user, the resistance parameter setter 37A sets the resistance parameters based on the set scaling coefficient.

In some embodiments, for each option displayed in the scaling coefficient input field 63 at the time of setting a scaling coefficient, corresponding resistance parameters are set in advance. That is, the storage section 35 stores the options for the scaling coefficient, which are displayed in the scaling coefficient input field 63, in association with the resistance parameters set in advance for each option. In some embodiments, a configuration may be adopted in which the user directly enters a numeral value to set the scaling coefficient.

In response to the user selecting a setting of the desired scaling coefficient from the options displayed in the scaling coefficient input field 63, the input/receiving section 34 receives the information. Then, the scaling coefficient setter 36 sets a scaling coefficient based on the information received by the input/receiving section 34 (S10A).

The resistance parameter setter 37A refers to the storage section 35 based on the set scaling coefficient to obtain resistance parameters associated with the scaling coefficient, and sets the obtained resistance parameters as the resistance parameters used for the settings of the resistance forces (S20A).

The resistance parameter setter 37A may determine, by other methods, the corresponding resistance parameters from the information related to the set scaling coefficient and may set the calculated resistance parameters as the resistance parameters used for setting the resistance forces.

According to the surgical robot 1A of some embodiments, the resistance parameter setter 37A sets the resistance parameters based on the scaling coefficient set by the user. This configuration makes the surgical robot easy to operate to set the resistance parameters.

The scaling coefficient is a parameter that is set depending on the contents of treatment and/or a surgical site. Therefore, by setting in advance the resistance parameters corresponding to the treatment and/or the surgery where each scaling coefficient is utilized, it is possible to set the resistance forces suitable for the treatment and/or the surgical site, thereby making the surgical robot easy to set up and operate.

The scaling coefficient and the resistance parameter may be set in advance for each user, and may be stored in the storage section 35 in association with the user information. Then, the resistance parameter setter 37 may set a resistance parameter by referring to the storage section 35 based on the user information received by the input/receiving section 34 and the set scaling coefficient. This configuration makes the surgical robot easy to make settings suitable for the user's operational feeling.

Figure 8:
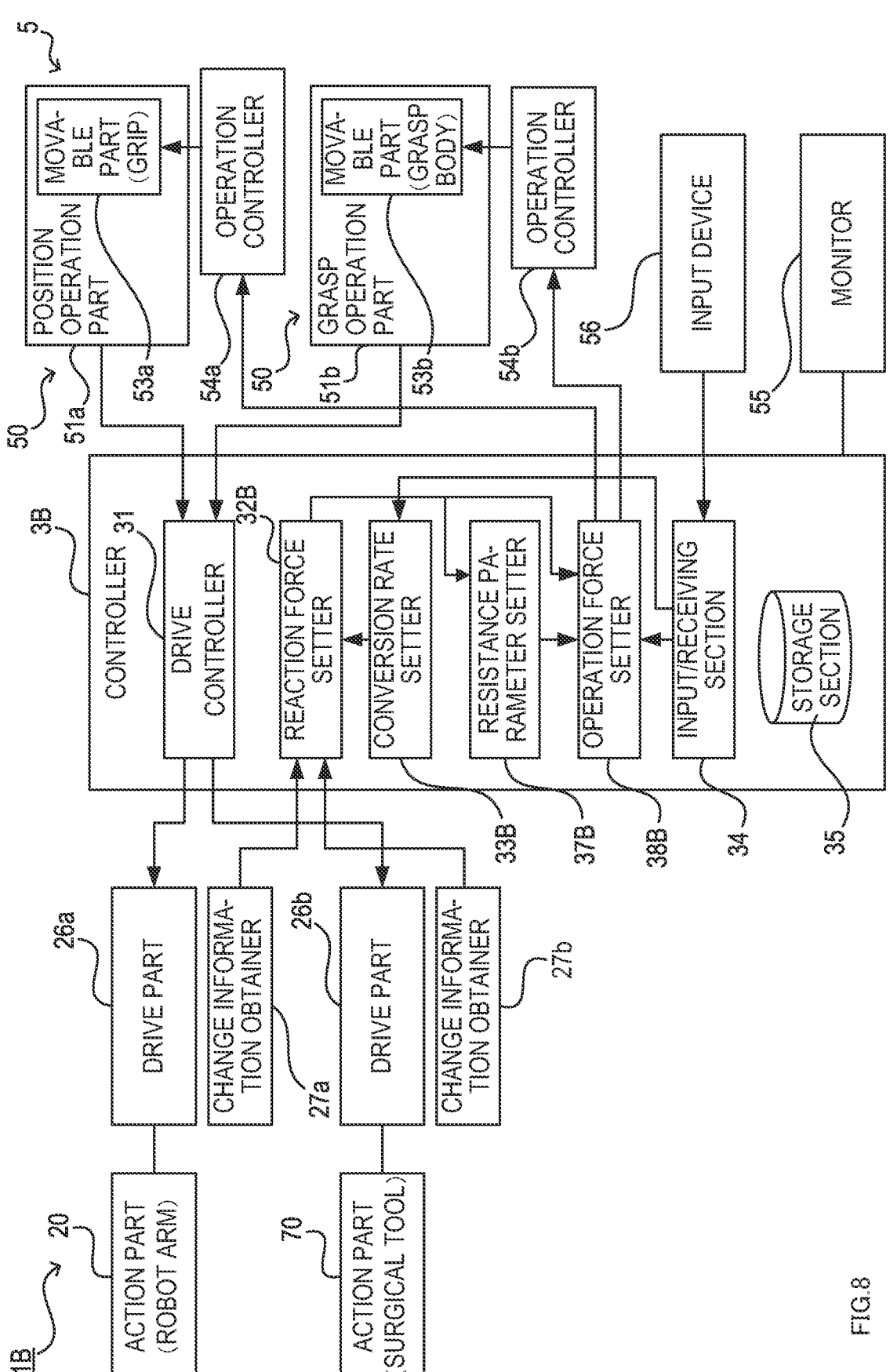
FIG. 8 is a block diagram of a surgical robot according to some embodiments.
Figure 9:
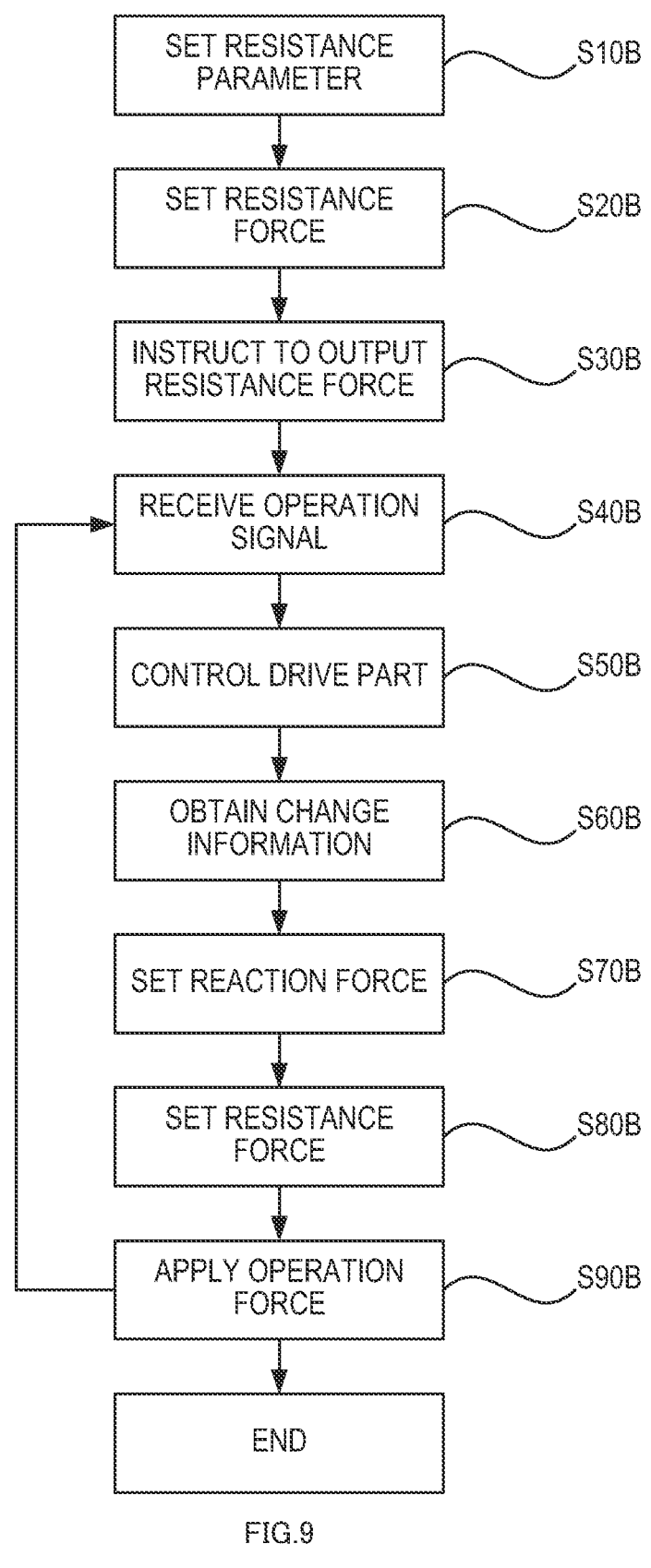
FIG. 9 is a flow diagram showing a process flow by a surgical robot according to some embodiments.

FIG. 8 is a block diagram of a surgical robot according to some embodiments, and FIG. 9 is a flow diagram showing a process flow by a surgical robot according to some embodiments.

Hereinafter, a surgical robot and a process flow will be described with reference to FIG. 8 and FIG. 9, respectively.

The basic structure of the surgical robot 1B is similar to the basic structure of the surgical robot 1 or the surgical robot 1A described above. However, a process to set the resistance parameter is different from the processes described in FIGS. 6 and 7. Thus, differences will be described with reference to FIG. 8 and FIG. 9, and the parts same as those of the processes described in FIGS. 6 and 7 will be denoted by the same reference numerals, and the descriptions thereof will be omitted for conciseness.

In the surgical robot 1B according to some embodiments, when the tip portion of the surgical tool 7, i.e. the grasper 71 or the like, is actuated while in contact with the tissue or the like of the patient, the surgical robot 1B has a function to make the user perceive, as "operation reaction force", a force corresponding to the force received by the tissue or the like of the patient due to the contact.

<Operation Reaction Force>

Hereinafter, a description will be made of an operation reaction force in some embodiments.

In general, when a treatment is performed using a surgical robot, the surgical robot is actuated according to the user's operation and a specified treatment is performed. This operation is done by the user's moving, in a desired direction and for a desired distance, the movable part whose position may be changed as the operation part is operated, i.e. the movable part that may be moved.

That is, as long as the user applies a force slightly larger than the operation force during movement to the movable part 53 of the operation part 51, the robot arm 2 and/or the surgical tool 7 is actuated in the direction according to the operation. In other words, even if, for example, the surgical tool 7 is already in contact with the tissue of the patient, the robot arm 2, the surgical tool 7 and/or another part continues to be actuated unless the user stops the operation of moving the movable part 53. If the robot arm 2, the surgical tool 7 and/or another part is actuated in this way, the surgical tool or the like will apply a force to the tissue of the patient with which the surgical tool is in contact.

Depending on the magnitude of the force applied to the tissue, the force may have an undesirable effect on the patient. Therefore, when the tip portion or another part of the surgical tool 7 applies a force to the tissue or the like of the patient, the surgical robot 1B according to some embodiments has a function to apply, to the movable part 53, a force corresponding to the magnitude of the force applied to the tissue of the patient, thereby making the user perceive the magnitude of the force applied to the tissue of the patient.

When the surgical tool 7 is moved and/or the grasper 71 is opened and closed in a state that the surgical tool 7 is not in contact with other parts, the drive part 26 outputs a certain driving force, thereby causing the action parts 20, 70 to perform specified actions. Hereinafter, this driving force is also referred to as "driving force during movement".

On the other hand, when the surgical tool 7 is in contact with the patient and the surgical tool 7 is to be moved further in a direction for contacting the tissue, the drive part 26 needs to output a force larger than the movement driving force to cause the action part 20 to perform the action. When the grasper 71 is closed to perform an action to grasp the tissue, the drive part 26 needs to output a force larger than the movement driving force to cause the action part 70 to perform the action. Hereinafter, the driving force outputted by the drive part 26 to further change the position of the surgical tool 7 or to close the grasper 71 to grasp the tissue in a state that the surgical tool 7 is in contact with the patient is referred to as "driving force during treatment". The force applied to the movable part 53 by the user to move the movable part 53 is referred to as "operation force during treatment".

The surgical robot 1B according to some embodiments has a function to determine that the surgical tool 7 is in contact with the tissue or the like of the patient and the surgical tool 7 is applying a force to the tissue or the like when the drive part 26 is outputting the driving force during treatment. In other words, the surgical robot 1B has a function to determine that the surgical tool 7 is in contact with the tissue or the like of the patient and applying a force to the tissue or the like in contact when the drive part 26 is outputting a force larger than the driving force during movement. In that case, the surgical robot 1B has a function that the reaction force setter 32B controls the operation controllers 54a, 54b to apply a force, which has a magnitude corresponding to the force applied by the surgical tool 7 to the tissue or the like of the patient, to the movable part 53 in the direction opposite to the operation direction.

If such a force is applied to the movable part 53, the user cannot move the movable part 53 when moving the movable part 53 unless the user applies a force larger than the operation force during movement to the movable part 53. This configuration allows the user to perceive that the surgical tool 7 is in contact with the patient or that the grasper 71 grasps the target tissue while operating the operation part 51. Also, the user may perceive the magnitude of the force applied by the surgical tool 7 or another part to the tissue or the like of the patient.

In some embodiments, the force applied by the operation controller 54a or 54b to the movable part 53 and having the magnitude corresponding to the force applied by the surgical tool 7 to the tissue or the like of the patient, in the direction opposite to the operation direction of the movable part 53, is also referred to as "operation reaction force". In other words, the force applied by the operation controller 54a or 54b to the movable part 53 in the opposite direction of the operation direction of the movable part 53 according to the increase in the driving force outputted by the drive part 26 is referred to as operation reaction force.

<1. Description of Configuration>

The robot arm 2B of the surgical robot 1B according to some embodiments further includes, as shown in FIG. 8, change information obtainers 27a, 27b. The change information obtainers 27a, 27b are air pressure sensors that measure the pressure of the compressed air of each of the pneumatic actuators configuring the drive parts 26a, 26b. In FIG. 8, the change information obtainers 27a, 27b, which respectively correspond to the drive parts 26a, 26b illustrated as examples, are shown as examples, and the descriptions of other change information obtainers 27a, 27b are omitted. Hereinafter, the change information obtainers 27a, 27b are also collectively referred to as a "change information obtainer 27".

The controller 3B includes, as shown in FIG. 8, the drive controller 31, a reaction force setter 32B, a conversion rate setter 33B, a resistance parameter setter 37B, an operation force setter 38B, the input/receiving section 34 and the storage section 35.

In some embodiments, the controller 3B is a computer system that includes hardware control logic, one or more microprocessors or one or more microcontrollers and has specialized software installed. That is, the specialized software and hardware (e.g., the hardware control logic, microprocessor, or microcontroller) cooperate to fulfill a function of each section, such as the drive controller 31, the reaction force setter 32B, the conversion rate setter 33B, the resistance parameter setter 37B, the operation force setter 38B, the input/receiving section 34 and the storage section 35. In the controller 3B, each section described below in detail may be configured of specialized hardware fulfilling its function.

The reaction force setter 32B is a part setting the magnitude of the operation reaction force based on the information obtained from the change information obtainer 27. The conversion rate setter 33B is a part setting a conversion coefficient used when the reaction force setter 32B sets the operation reaction force.

The resistance parameter setter 37B is a part setting a resistance parameter that is a coefficient used when the resistance force is set. The resistance parameter setter 37B sets the resistance parameter based on the information related to the resistance parameter inputted by the user and the operation reaction force set by the reaction force setter 32B.

The operation force setter 38B is a part setting the magnitudes of the forces applied by the operation controllers 54a, 54b to the movable parts 53. In other words, the operation force setter 38B is a part setting the magnitudes of the operation force during movement and the operation force during treatment. The operation force setter 38B is a part causing the operation controller 54a, 54b to each output a force having a magnitude obtained by adding the resistance force that is set based on the resistance parameter and the operation reaction force set by the reaction force setter 32B.

<2. Details of Control>

A description will be made of the control of the surgical robot 1B of some embodiments with reference to FIG. 9. The resistance parameter setter 37B sets each of the resistance parameters based on the information received by the input/receiving section 34 (S10B). A description will be made of a case where the resistance parameter setter 37B sets $k_{1a}$ as a resistance parameter for the resistance force applied to the position operation part 51a and sets $k_{1b}$ as a resistance parameter for the resistance force applied to the grasp operation part 51b. Each of the resistance parameters $k_{1a}$, $k_{1b}$ is a real number of value that is equal to or greater than 0 and less than 1.

The conversion rate setter 33B sets a conversion coefficient based on the information received by the input/receiving section 34. A description will be made of a case where $k_{ha}$ is set as a conversion coefficient corresponding to the operation reaction force applied to the position operation part 51a, i.e. the grip 53a, and $k_{hb}$ is set as a conversion coefficient corresponding to the operation reaction force applied to the grasp operation part 51b, i.e. the grasp body 53b. Here, each of the conversion coefficients $k_{ha}$, $k_{hb}$ is a real number that is equal to or greater than 0.

The operation force setter 38B sets the magnitudes of the resistance forces based on the resistance parameters set by the resistance parameter setter 37B, i.e. based on $k_{1a}$ and $k_{1b}$ (S20B). In some embodiments, a description will be made of an example in which the operation force setter 38 sets $F_{0a}$ ($=k_{1a} \times F_a$) as the resistance force applied to the position operation part 51a and sets $F_{0b}$ ($=k_{1b} \times F_b$) as the resistance force applied to the grasp operation part 51b. Here, $F_a$ and $F_b$ are forces each having a specified magnitude that serves as a reference when setting the resistance forces. However, in other embodiments, the operation force setter 38B may set the resistance forces based on the resistance parameters set by the resistance parameter setter 37B in a manner different from the above.

The operation force setter 38B outputs signals to the operation controllers 54a, 54b to cause them to output the set resistance forces (S30B).

In response to the user operating the position operation part 51a and the grasp operation part 51b, the position operation part 51a and the grasp operation part 51b output operation signals according to the operation to the drive controller 31. For example, the user applies a force larger than the force $F_{0a}$ ($=k_{1a} \times F_a$) to the grip 53a to operate the grip 53a. The user also applies a force larger than the force $F_{0b}$ ($=k_{1b} \times F_b$) to the grasp body 53b to operate the grasp body 53b.

In response to the operation signals being inputted (S40B), the drive controller 31 outputs signals to cause the corresponding drive part 26 to be actuated based on the inputted operation signals. That is, the drive controller 31 controls the corresponding drive part 26 to cause the action part 20 and the action part 70 to perform actions according to the user's operation (S50B).

When the surgical tool 7 is moved and the grasper 71 on the tip side of the shaft 73 is brought into contact with the tissue of the patient, for example, the drive part 26 outputs a driving force larger than the movement driving force in order for actions according to the operation signal.

The drive part 26a will be specifically described as an example. The drive part 26a outputs a driving force larger than the movement driving force to the corresponding action part 20 to cause it to perform an action based on the operation signal. That is, additional compressed air is supplied from an unillustrated pressure generator, whereby the pressure of the drive part 26a is increased.

The same may be applied to the drive part 26b, and in response to the user closing the grasper 71 to perform an action of grasping the target tissue and the jaw 72a and the jaw 72b being brought into contact with the target tissue, the drive part 26b outputs a driving force larger than the movement driving force in order to perform the grasping action. That is, additional compressed air is supplied from an unillustrated pressure generator, whereby the pressure of the drive part 26b is increased.

The reaction force setter 32B detects changes in pressure of the driver 26a and the driver 26b based on information from the change information obtainers 27a, 27b (S60B). Specifically, the reaction force setter 32B detects an amount of change in pressure of each of the drive parts 26a and 26b when the pressures of the drive parts 26a and 26b are increased compared to the pressures of the drive parts 26a and 26b outputting the movement driving forces.

The information about the changes in pressure of the drive parts 26a, 26b detected by the change information obtainers 27a, 27b is one example of change information. A description will be made of an example in which the amount of change of the drive part 26a is $\Delta P_a$, and the amount of change of the drive part 26b is $\Delta P_b$.

When detecting the changes of the drive parts 26a, 26b, the reaction force setter 32B performs a process of setting the operation reaction forces (570B). Specifically, the reaction force setter 32 sets the values, as the operation reaction forces, obtained by multiplying the amounts of change in pressure, which are acquired based on the signals from the change information obtainers 27a, 27b, by the conversion coefficients set by the conversion rate setter 33B.

The reaction force setter 32B sets each of the operation reaction forces based on the set conversion coefficient. Specifically, the reaction force setter 32B sets $F_{ha}$ (=$\Delta P_a \times k_{ha}$) as the operation reaction force applied to the position operation part 51a, i.e. the grip 53a. The reaction force setter 32B also sets $F_{hb}$ (=$\Delta P_b \times k_{hb}$) as the operation reaction force applied to the grasp operation part 51b, i.e. the grasp body 53b.

In response to the operation reaction forces being set by the reaction force setter 32B, the resistance parameter setter 37B sets resistance parameters based on the information about the set operation reaction forces. A description will be made of an example in which when the operation reaction forces are set by the reaction force setter 32B, the resistance parameter setter 37B sets the resistance parameters to "0".

That is, a description will be made of an example in which the resistance parameters are set so that only the operation reaction forces $F_{ha}$ and $F_{hb}$ are applied to the operation part 51 by the operation controllers 54a, 54b. In other words, a description will be made of an example in which the resistance parameters are set so that the operation forces during treatment are the operation reaction force $F_{ha}$ and the operation reaction force $F_{hb}$. If the resistance parameters are set in this way, the user may precisely perceive the force applied by the surgical tool 7 or another part to the patient.

When the operation reaction forces are set, the resistance parameter setter 37B may set the resistance parameters each having the magnitude equal to or greater than "0". That is, the resistance parameter may be set so that the operation force during treatment is a force having the magnitude obtained by adding the operation reaction force and the resistance force. This configuration allows the user to perform an operation for the treatment while obtaining a desired certain operational feeling.

For example, when the operation reaction force is set, the resistance parameter setter 37B may set a resistance parameter having a specified magnitude and then the value of the resistance parameter may be set to decrease as the value of the operation reaction force increases.

In this configuration, as the operation reaction force increases, the resistance force decreases. Thus, the surgical robot makes the user to perceive the force applied by the surgical tool 7 or another part to the tissue of the patient more easily as the force applied by the surgical tool 7 or another part to the tissue of the patient increases.

In some embodiments, when the operation reaction force is set, the resistance parameter setter 37B may set a resistance parameter having a specified magnitude and then the value of the resistance parameter may be set to increase as the value of the operation reaction force increases.

In this configuration, as the force applied by the surgical tool 7 or another part to the tissue of the patient increases, the resistance force also increases, whereby it may be expected that the user may easily perceive that a force is applied to the tissue of the patient.

In some embodiments, when the reaction forces are set, the resistance parameter setter 37B may set resistance parameters each having a certain magnitude of equal to or greater than "0". In some embodiments, the resistance parameter setter 37B may set, in a manner different from the above, the resistance parameters based on the reaction force $F_{ha}$ and the reaction force $F_{hb}$.

In response to the resistance parameter setter 37B setting the resistance parameters, the operation force setter 38B sets the magnitudes of the resistance forces based on the set resistance parameters (S80B). In some embodiments, since the resistance parameter setter 37B sets the resistance parameters to "0", the operation force setter 38B sets the resistance force applied to the position operation part 51a to "0" and sets the resistance force applied to the grasp operation part 51b to "0".

Furthermore, the operation force setter 38B outputs signals to the operation controllers 54a, 54b to cause them to output forces each having the magnitude obtained by adding the set resistance force and the reaction force (S90B). In some embodiments, since each of the resistance forces is set to "0", the operation force setter 38B controls the operation controller 54a to apply the reaction force $F_{ha}$ to the position operation part 51a, i.e. the grip 53a in the direction opposite to the operation direction. The operation force setter 38B also controls the operation controller 54b to apply the reaction force $F_{hb}$ to the grasp operation part 51b, i.e. the grasp body 53b in the direction opposite to the operation direction.

In response to the user performing an operation to move the surgical tool 7 in a direction in which the contact between the grasper 71 and the target tissue are separated, the drive controller 31B controls the corresponding drive part 26a to restore the outputting driving force to the driving force during movement. That is, the drive controller 31B performs control to reduce the pressure of the drive part 26a.

In some embodiments, in response to the user performing an operation to open the grasper 71 to release the grasped target tissue, the drive controller 31B controls the corresponding driver 26b to restore the outputting driving force to the driving force during movement. That is, the drive controller 31B performs control to reduce the pressure of the drive part 26b.

In this case, since a difference in pressure from the driving force during movement, i.e. the amount of change is 0 for both $\Delta P_a$ and $\Delta P_b$, the reaction force setter 32B sets the operation reaction force applied to the position operation part 51a, i.e. the grip 53a to "0" and sets the operation reaction force applied to the grasp operation part 51b to "0" (S70B).

In response to the operation reaction forces being set to "0" by the reaction force setter 32B, the resistance parameter setter 37B sets the resistance parameters based on the information about the set operation reaction forces. The resistance parameter setter 37B newly sets $k_{1a}$ as a resistance parameter for the resistance force applied to the position operation part 51a and sets $k_{1b}$ as a resistance parameter for the resistance force applied to the grasp operation part 51b.

Then, based on the set resistance parameters $k_{1a}$, $k_{1b}$, resistance forces $F_{0a}$ ($=k_{1a} \times F_a$) and $F_{0b}$ ($=k_{1b} \times F_b$) are set and applied to the position operation part 51a and the grasp operation part 51b.

When the above operations are repeated and the treatment is completed, the process is terminated according to a specified operation by the user.

With the above-described surgical robot 1B, the magnitude of the resistance force is set according to the operation reaction force that is set when the surgical tool 7 is brought into contact with the tissue or the like of the patient and the drive part 26 outputs a force larger than the driving force during movement. Therefore, in a state where the surgical tool 7 is not in contact with the tissue of the patient, the user may perform an operation with a desired operational feeling. In a state where the surgical tool 7 is in contact with the patient's target tissue, i.e. when performing a treatment or the like, the user may obtain an operational feeling according to the magnitude of the force applied to the patient. That is, the magnitude of the resistance force when performing a treatment may be set depending on the site and the state of the target tissue and/or the contents of the treatment. Therefore, it is possible to provide a surgical robot that is easy to operate and that furthermore allows to perform a treatment suitable for the site and the state of the target tissue.

The operation reaction force is set based on the amount of change in the output of the drive part 26. Thus, the user may appropriately know the magnitude of the force received by the tissue or the like of the target site due to the user's operation while operating the surgical robot. In other words, the user may perceive the magnitude of the force received by the tissue or the like of the target site by the user's own hand performing the operation. This configuration allows the user to operate considering the magnitude of the force applied by the surgical part 7 or another part to the tissue or the like of the patient while operating with the desired operational feeling. Therefore, it is possible to provide a surgical robot that is easy to operate and that furthermore allows to perform a treatment suitable for the site and/or the state of the target tissue.

The technical scope of the present disclosure is not limited to the above embodiments, and various modifications may be made without departing from the gist of the disclosure. For example, in the above-described embodiments, the description has been made of a configuration in which the pneumatic actuators are used in the operation controllers 54a, 54b; however, a configuration may also be adopted in which electric actuators or electric motors are used. In this case, for the change information obtainers 27a, 27b, power sensors, ammeters, or other devices detecting the power or current supplied to the electric motor may be used. A configuration may also be adopted in which the reaction force setter 32B calculates the amount of change in the driving force outputted by the drive part 26 based on the amount of change in electricity supplied to the drive part 26, thereby setting the operation reaction force based on the calculated value.

In the above-described embodiments, the description has been made of a case where the surgical tool 7 is a pair of forceps; however, the surgical tool 7 is not limited to the pair of forceps. The surgical tool 7 may be, for example, an electric scalpel, a stapler, or another tool that is used in endoscopic surgery and that is arranged at the tip side of the shaft 73.

In the above-described embodiments, the description has been made of a case where the surgical robot 1 is used in endoscopic surgery; however, the field in which the surgical robot 1 is used is not limited to the endoscopic surgery. For example, the surgical robot 1 may be used in other fields of surgery or treatment for patients, such as neurosurgery or cardiovascular surgery.

For example, for each field and/or target site of surgery in which the surgical robot 1 is used, the corresponding resistance parameters and conversion coefficients may be set in advance, and combinations of the field and/or target site of surgery and the corresponding resistance parameters and conversion coefficients set in advance may be stored in the storage section 35. The conversion rate setter 33B may then refer to the storage section 35 based on the information about the field and/or target site of surgery, which is received by the input/receiving section 34, and acquire the corresponding conversion coefficients and resistance parameters to set. In this way, simply by, for example, selecting the target site on which the surgery is to be performed and/or the field of surgery, the resistance parameters and the conversion coefficients suitable for the site and/or the field of surgery may be set, making the surgical robot easy to make settings.

In some embodiments, the resistance parameters and the conversion coefficients may be set in advance for each user, and a combination of the user information about the user and the resistance parameters and the conversion coefficients set in advance may be stored in the storage section 35. The conversion rate setter 33B may then refer to the storage section 35 based on the information about the user information, which is received by the input/receiving section 34, and acquire the combination of the corresponding resistance parameters and the conversion coefficients to set. In this way, simply by entering the user's own information, the resistance parameters and the conversion coefficients suitable for the user may be set, thereby making the surgical robot easy to set up.

Various embodiments have been described above with reference to the drawings. However, it is to be understood that the present disclosure is not limited to the above embodiments, but various changes and modifications may be made therein without departing from the spirit and scope thereof as set forth in appended claims.

The invention claimed is:

1. A surgical robot comprising:
an operation part that includes a movable part moved by a force applied by an operation by a user, the movable part including a grasp body that is rotatable, and a grip;
a grasper that performs an action according to the operation;
an actuator that supplies a driving force to the grasper;
an operation controller that controls a movement of the movable part; and a controller configured to implement:

a resistance parameters setter that sets a first resistance parameter value for the grasp body and a second resistance parameter value for the grip, and an operation force setter that sets a first magnitude of a first resistance force for the grasp body, based on the first resistance parameter value, and sets a second magnitude of a second resistance force for the grip, based on the second resistance parameter value, the first resistance force and the second resistance force being forces in directions opposite to directions of the movement of the grasp body and the grip of the movable part, respectively, wherein the operation controller applies, to the grasp body of the movable part, the first resistance force having the first magnitude set by the operation force setter, and applies, to the grip of the moveable part, the second resistance force having the second magnitude set by the operation force setter, wherein the actuator actuates the grasper based on at least one of a first operation force applied by an operation of the grasp body by the user being greater than the first magnitude of the first resistance force applied to the grasp body or a second operation force applied by an operation of the grip by the user being greater than the second magnitude of the second resistance force, wherein the controller is further configured to implement a scaling coefficient setter that sets a scaling coefficient that is a ratio between a first distance of movement of the movable part and a second distance of corresponding movement of the grasper, and wherein the operation force setter sets the first magnitude of the first resistance force and the second magnitude of the second resistance force based on the first resistance parameter value and the second resistance parameter value that are set based on the scaling coefficient.

2. The surgical robot according to claim 1, wherein the controller is further configured to implement an input section that receives an input of information to set the first resistance parameter value and the second resistance parameter values, wherein the operation force setter sets the first magnitude of the first resistance force and the second magnitude of the second resistance force based on the first resistance parameter value and the second resistance parameter value that are set based on information received by the input section.

3. The surgical robot according to claim 1, wherein the controller is further configured to implement a reaction force setter that sets magnitudes of operation reaction forces, the operation reaction forces corresponding to the driving force and being forces in a direction opposite to the direction of the movement of the grasp body and the grip of the movable part, the reaction force setter setting the magnitudes of the operation reaction forces based on change information about a change in the driving force supplied by the actuator when the grasper is actuated according to the operation, wherein the operation force setter sets the first magnitude of the first resistance force and the second magnitude of the second resistance force based on the first resistance parameter value and the second resistance parameter value, respectively, and wherein the operation controller applies, to the grasp body and the grip, forces obtained by adding the resistance forces having the magnitudes set by the operation force setter and the operation reaction forces having the magnitudes set by the reaction force setter.

4. The surgical robot according to claim 1, wherein the controller is configured to implement an input section that receives input of user information about the user and a storage section that stores the first resistance parameter value and the second resistance parameter value that are set for each user so as to be associated with the user information, wherein the operation force setter refers to the storage section and sets the first magnitude of the first resistance force based on the first resistance parameter value associated with the user information received by the input section and sets the second magnitude of the second resistance force based on the second resistance parameter value associated with the user information received by the input section.

5. The surgical robot according to claim 1, wherein:

the operation part is provided in plural; and the grasper is provided in plural corresponding to the plurality of operation parts, wherein the operation force setter sets magnitudes of each resistance force for each of the plurality of operation parts.

6. A controller of a surgical robot that controls the surgical robot including an operation part having a movable part that is moved by an operation performed by a user, the movable part including a grasp body that is rotatable, and a grip, and a grasper that performs an action according to the operation, the controller comprising at least one microprocessor configured to:

set a first resistance parameter value for the grasp body and a second resistance parameter value for the grip;

set magnitudes of resistance forces for each of the grasp body and the grip, based on the first resistance parameter value for the grasp body and second resistance parameter value for the grip, respectively, the resistance forces being in a direction opposite to a direction of the movement of the grasp body and the grip of the movable part, respectively; and control the movement of the grasp body and the grip of the movable part to apply, to the operation part, the resistance forces having the magnitudes, and control movement of the grasper according to the operation based on operation forces of the operation performed by the user on the movable part being greater than the resistance forces having the magnitudes, wherein the at least one microprocessor is further configured to:

set a scaling coefficient that is a ratio between a first distance of movement of the movable part and a second distance of corresponding movement of the grasper, and set the magnitudes of the resistance forces based on the first resistance parameter value and the second resistance parameter value that are set based on the scaling coefficient.

7. A surgical robot comprising:

an operation device comprising a grasp body and a grip, the operation device being movable to perform an operation by a force applied to the operation device;

a first actuator that controls a movement of the grip of the operation device;

a robot arm on which the operation device is provided;

a second actuator that supplies a driving force to the robot arm; and a controller configured to set a first resistance parameter value for the grasp body and a second resistance parameter value for the grip, and to set magnitudes of resistance forces for each of the grasp body and the grip, based on the first resistance parameter value that is set for the grasp body and the second resistance parameter value that is set for the grip, respectively, the resistance forces being in a direction opposite to a direction of the movement of the grasp body and the grip of the operation device, respectively, wherein the first actuator applies, to the grasp body and the grip of the operation device, the resistance forces having the magnitudes, respectively, set by the controller, wherein the second actuator supplies, to the robot arm, the driving force to actuate the robot arm based on operation forces applied to the grasp body and the grip of the operation device being greater than the resistance forces having the magnitudes, respectively, and wherein the controller is further configured to:

set a scaling coefficient that is a ratio between a first distance of movement of the operation device and a second distance of corresponding movement of the robot arm, and set the magnitudes of the resistance forces based on the first resistance parameter value and the second resistance parameter value that are set based on the scaling coefficient.

8. The surgical robot according to claim 7, wherein the controller is further configured to receive information for setting the first resistance parameter value and the second resistance parameter value, and wherein the first resistance parameter value and the second resistance parameter value are set based on the information.

9. The surgical robot according to claim 7, wherein the controller is further configured to set a magnitude of a reaction force that corresponds to the driving force and that is in a direction opposite to the first direction of the movement of the operation device, based on change information about a change in the driving force, and wherein the first resistance parameter value and the second resistance parameter value are set based on the magnitude of the reaction force.

10. The surgical robot according to claim 7, wherein the surgical robot further comprises a storage that stores specific resistance parameter values that are set for each user of a plurality of users in association with user information of the user, the controller is configured to receive user information, and read the resistance parameter values associated with a user corresponding to the user information, and the controller sets the magnitudes of the resistance forces based on each of the resistance parameter values.

11. The surgical robot according to claim 7, wherein:

the operation device is provided in plural; and the controller sets the magnitudes of the resistance forces for each of the plurality of operation devices.

12. The surgical robot according to claim 7, wherein the first actuator is a pneumatic actuator.

13. The surgical robot according to claim 1, wherein the actuator is a pneumatic actuator.

14. The surgical robot according to claim 1, wherein the grip is movable in three dimensions.

15. The surgical robot according to claim 1, wherein the operation part comprises a support body, wherein the grasp body is rotatable with respect to the support body to change an angle therebetween.

16. The surgical robot according to claim 7, wherein the operation device comprises a support body, wherein the grasp body is rotatable with respect to the support body to change an angle therebetween.

17. The surgical robot according to claim 1, wherein each resistance parameter value has a certain magnitude of equal to or greater than 0.

18. The surgical robot according to claim 1, wherein the actuator actuates the grasper to open/close based on the first operation force applied by the operation of the grasp body by the user being greater than the first magnitude of the first resistance force applied to the grasp body, and actuates the grasper to move positionally based on the second operation force applied by the operation of the grip by the user being greater than the second magnitude of the second resistance force.

* * * * *